(12) United States Patent
Blackstone et al.

(10) Patent No.: US 7,836,097 B2
(45) Date of Patent: Nov. 16, 2010

(54) EXTENSIBLE DATABASE SYSTEM AND METHOD

(75) Inventors: Eugene H. Blackstone, Cleveland Heights, OH (US); William H. Stellhorn, Lyndhurst, OH (US); Chimezie Thomas-Ogbuji, Shaker Heights, OH (US); Christopher Pierce, Shaker Heights, OH (US); Peter Kisuule, North Ridgeville, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 382 days.

(21) Appl. No.: 11/788,126

(22) Filed: Apr. 19, 2007

(65) Prior Publication Data

US 2007/0198564 A1 Aug. 23, 2007

Related U.S. Application Data

(63) Continuation-in-part of application No. 11/238,536, filed on Sep. 29, 2005.

(60) Provisional application No. 60/614,442, filed on Sep. 29, 2004.

(51) Int. Cl.
G06F 7/00 (2006.01)
(52) U.S. Cl. .................................. 707/803
(58) Field of Classification Search ............. 707/100, 707/803
See application file for complete search history.

(56) References Cited

U.S. PATENT DOCUMENTS

| 5,768,578 | A | 6/1998 | Kirk et al. |
| 6,640,231 | B1 | 10/2003 | Andersen et al. |
| 2002/0073080 | A1* | 6/2002 | Lipkin ......................... 707/3 |
| 2004/0117395 | A1 | 6/2004 | Gong et al. |
| 2005/0262489 | A1 | 11/2005 | Streeter et al. |
| 2007/0198564 | A1 | 8/2007 | Blackstone et al. |

OTHER PUBLICATIONS

Berners-Lee et al., "The Semantic Web", *Scientific America*, May 2001, pp. 35-43.
Brachman, "Systems that Know What They're Doing: The New DARPA/IPTO Initiative in Cognitive Systems", *DARPAtech 2002 Conference*, Jul. 2002.
McGuinness et al. (Editors), "OWL Web Ontology Language Overview", W3C Recommendation Feb. 10, 2004, http://www.w3.org/TR/2004/REC-owl-features-20040210.
Mills•Davis, "Semantic Wave 2006 Part-1: Executive Guide to Billion Dollar Markets", A Project10X Special Report, pp. 1-55, Jan. 2006.

(Continued)

*Primary Examiner*—Etienne P LeRoux
*Assistant Examiner*—Ajith Jacob
(74) *Attorney, Agent, or Firm*—Tarolli, Sundheim, Covell & Tummino LLP (57) ABSTRACT

A system includes a metadata model arranged to express concepts in a domain as a domain model. The domain model includes domain elements and at least one hierarchical relationship between domain elements. The system also includes at least one given instance representation of the domain model, which includes instance data stored in a repository. A user interface is associated with the domain model and configured to at least create, view and modify at least one given instance representation of the domain model.

35 Claims, 8 Drawing Sheets

OTHER PUBLICATIONS

Fielding et al., "Four Ontological Models for Radiological Diagnostics", Studies in Health Technology and Informatics, vol. 124, pp. 761-766, Aug. 2006.

Kumar, "Towards the Use of Ontologies for Activity-Based Costing in Healthcare Organizations", Aug. 2006.

Ceusters et al., "A Realism-Based Approach to the Evolution of Biomedical Ontologies", *AMIA Symp.*, Nov. 2006.

Ceusters et al, "Strategies for Referent Tracking in Electronic Health", Journal Biomedical Informatics, Jun. 2006.

Staab et al., "Semantic Community Web Portals", *Computer Networks*, vol. 33, No. 1-6, Jun. 1, 2000, pp. 473-491, XP004304786.

Hartel et al., "Modeling a Description Logic Vocabulary for Cancer Research", *Journal of Biomedical Informatics*, vol. 38, No. 2, Apr. 1, 2005, pp. 114-129, XP004816947.

Ogbuji et al., "Case Study: A Semantic Web Content Repository for Clinical Research", *Semantic Web Use Cases and Case Studies*, Oct. 2007, pp. 1-4, XP002495444.

Shieh et al., "A Reasoning Framework for Heterogeneous XML", *Information Technology: Research and Education, 2003, Proceedings. ITR E2003*. IEEE, Aug. 11, 2003, pp. 404-411, XP010685481.

Hu, Metadata-Driven Framework of Management of Information Resources in Railway Industry, *Geoscience and Remote Sensing Symposium*, 2004. IGARSS '04. Proceedings. IEEE, vol. 5, Sep. 20, 2004, pp. 2929-2932, XP010752374.

\* cited by examiner

EXTENSIBLE DATABASE SYSTEM AND METHOD

RELATED APPLICATIONS

This application is a continuation-in-part of U.S. patent application Ser. No. 11/238,536, which was filed on Sep. 29, 2005, and entitled EXTENSIBLE METADATA-DRIVEN, SELF-ORGANIZING, GENERAL PURPOSE DATA MANAGEMENT SYSTEM WITH DYNAMIC USER INTERFACES, which claims the benefit of U.S. Provisional Patent Application No. 60/614,442, which was filed on Sep. 29, 2004, and entitled EXTENSIBLE METADATA-DRIVEN, SELF-ORGANIZING GENERAL PURPOSE DATA MANAGEMENT SYSTEM WITH DYNAMIC USER INTERFACES, the entire contents of each of the above-identified applications being incorporated herein by reference.

BACKGROUND

A central concept of a database is to collect organized information and knowledge. Various types of databases and database management systems have been developed and are being developed. Typically, a database has a structural description of information and knowledge held in that database, known as a schema. The schema describes the information and knowledge represented in the database and their relationships. Most database management systems are built around one particular way a database is organized.

The choice of database organization associated with stored data tends to vary according to the type of information being represented. As an example, effective and efficient management of computerized data for scientific applications, including medical data of all kinds, has proven more difficult, in general, than effective management of data in more common, transaction-oriented business applications such as banking, accommodation reservations, on-line purchasing, and the like. Unlike commercial databases, scientific databases often hold a wider spectrum of kinds or types of data. For example, a single dataset may be retained in several forms: raw data as collected; calibrated data corrected for experimental conditions; validated data corrected for known errors; derived products such as graphs and computed values; complex 2D, 3D, 4D, and color-coded visualizations; and interpreted data as represented with respect to various models. Further, information retrieval from scientific data tends to be ad hoc and exploratory in nature, oriented toward a particular question at hand that was not necessarily anticipated at a time that such data were collected. This type of usage is not consistent with the high volume processing of predefined, stored transactions frequently found in business applications. For scientific data to be processed in a meaningful way, it is often essential to record and preserve associated metadata (data about the data) such as operating characteristics and calibration information for particular measuring instruments, ambient conditions when measurements were made, etc. Popular database organizations, including relational, do not work well with requirements such as these.

For one particular example, information in patients' medical records shares the above characteristics of scientific data. In particular, medical information features numerous and often-changing interdependencies among variables and a need for sophisticated processing of temporal information. The situation is aggravated by the ongoing explosive growth in medical knowledge, which implies the continual incorporation of new data elements, new structural components, and new relationships among data elements within a database.

Maintaining databases in view of these deficiencies can come at a substantial cost. In many existing database management systems, adding a new data element or a new structural component to an existing database requires services of an expert database administrator and computer programmer and often necessitates restructuring of a relational database to meet changing needs of analysis.

Many of these deficiencies can be eliminated by incorporation of a knowledgebase with the database, which facilitates storage and retrieval of knowledge, for the purpose of automated reasoning about the data. The knowledgebase consists of data and rules that describe relationships among knowledge elements that are logically consistent. These data and rules are expressed in a particular knowledge representation.

A related ongoing effort relates to the creation of a semantic web. The semantic web is a project that seeks to create a universal medium for information exchange by putting documents with computer-processable meaning (semantics) on the World Wide Web. This approach seeks to leverage descriptive technologies, the Resource Description Framework (RDF) and Web Ontology Language (OWL), and the data-centric, customizable Extensible Markup Language (XML) to provide descriptions that can supplement or replace the content of Web documents. A goal of the semantic web is to enhance the machine-readability of web content by adding meaning (semantics) to the content, so as to facilitate automated information gathering, reasoning and research by computers.

SUMMARY

The present invention relates to an extensible knowledgebase/database system and method.

One aspect of the present invention provides a database system that includes a metadata model arranged to express concepts in a domain, or area of interest, hereafter called "domain model." A domain model includes domain elements and at least one hierarchical relationship between domain elements. There can be one or more instances of the domain model, consisting of "instance data." One domain model describes how instance data are organized in a repository. A user interface is associated with the domain model and is configured to create, modify and extend it. The system can be programmed to generate one or more tools automatically that enable a user (e.g., a domain expert) to manage instance data without requiring assistance of a database expert.

Another aspect of the present invention provides a method for providing an extensible database. The method includes storing a metadata model programmed to express concepts in a given domain as a domain model. The stored metadata defines at least one hierarchical relationship between data elements in the domain model. Predetermined rules for interpreting the stored metadata are also stored. At least a portion of the domain model is instantiated as a domain instance. The domain model is extensible and is independently changeable from the stored instance data.

Yet another aspect of the present invention provides a knowledgebase/database system that is independent of the physical storage system. This is because the present invention uses domain instance representations (such as RDF and XML) that are independent of physical storage.

DETAILED DESCRIPTION

The present invention relates to an extensible database system and method. It provides an approach to manage efficiently disparate and constantly changing database models and instance data as are often found in domains for various enterprises. The approach described herein enables a domain expert to modify or extend the domain model and instance data without requiring the assistance of a database expert.

Figure 1:
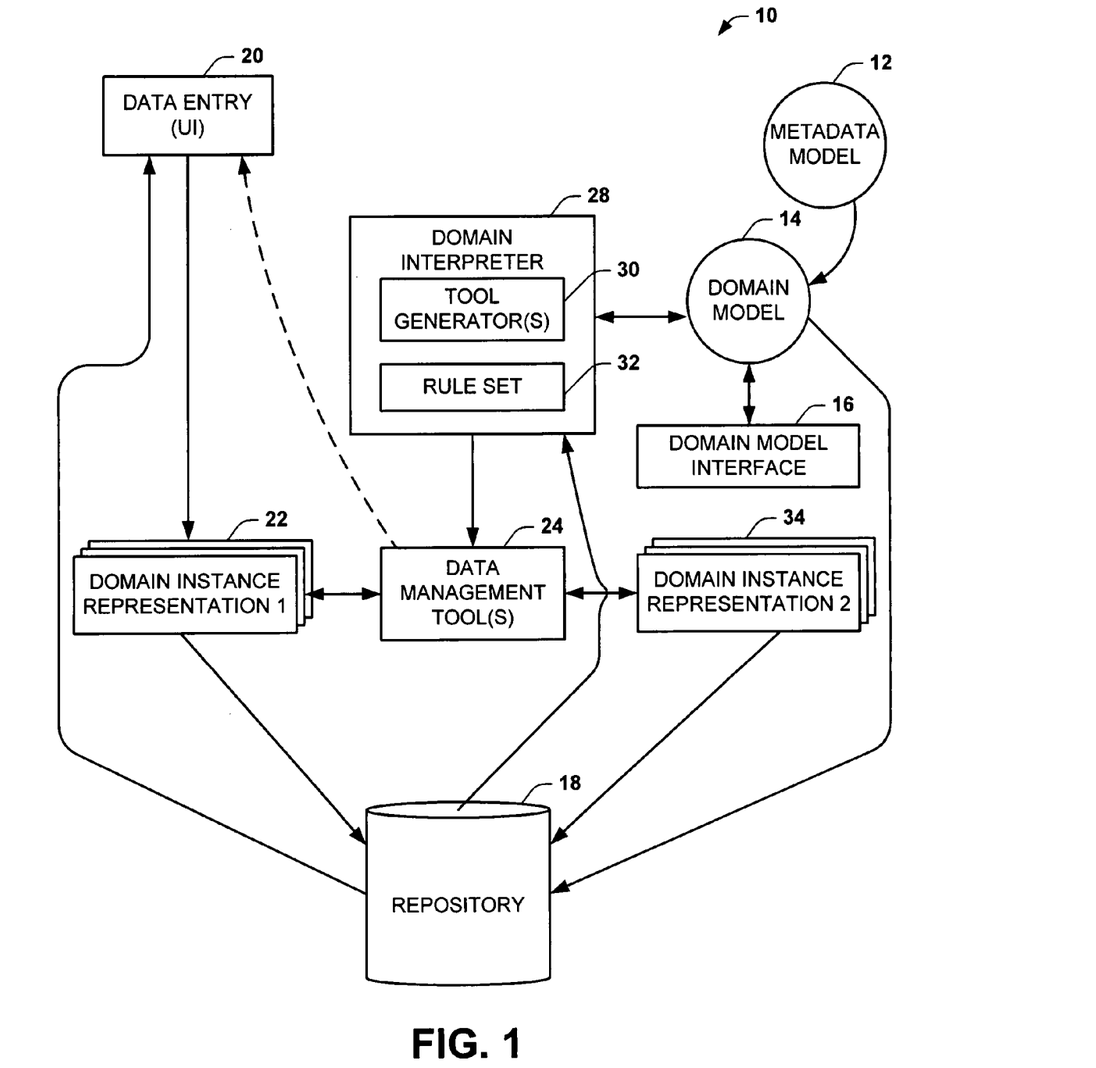
FIG. 1 depicts an example of a database system that can be implemented according to an aspect of the present invention.

FIG. 1 depicts an example of a system 10 that can be implemented in accordance with an embodiment of the present invention. System 10 includes a metadata model 12 that can be utilized to express concepts in one or more domains as a corresponding domain model 14. As described herein, domain model 14 is extensible and may be modified according to requirements of the domain concepts being represented. Each of the models 12 and 14 can be represented in a knowledge representation language, such as the Resource Description Framework (RDF). It will be appreciated that the domain model 14 can be represented in various syntactic forms, such as RDF/XML, Notation3 (N3), and the like. As used herein, the term data generally refers to organized values for variables, such as may be expressed symbolically (e.g., as numbers, characters or images). For example, data can consist of one or more propositions that reflect reality, such as may take the form of measurements or observations of a variable. The term knowledge is intended to encompass the synthesis of information, data and analyses as can be arrived at by inductive reasoning. Typically, new knowledge is assimilated within the body of existing knowledge, such as can occur in the form of inferences, speculations and hypotheses. As described herein, the system 10 thus can be considered a combination database and knowledgebase.

The domain model 14 includes data elements and can be conceptually envisioned as a polyhierarchical graph. For example, the data elements in the domain model express knowledge in a domain using a formal knowledge representation. As one example, the formal knowledge representation can be in the form of predicate logic, such as is often in the form of sentences and terms employed by first order predicate logic (FOPL) and its derivative languages. These sentences are often persisted (stored) as graph data structures, with nodes consisting of terms and directed connecting arcs representing the sentences. The domain model 14 includes metadata that defines or describes the relationships between the data elements. The metadata within the domain model 14 can also define other properties, such as (but not limited to) the type of data element, purpose of a data element, and constraints of a data element.

As a further example, the data elements in the domain model 14 can be identified via resolvable uniform resource identifiers (URIs), such that the data elements can be easily accessed in the enterprise (e.g., via an intranet or the Internet) implementing the system 10. URIs facilitate linking (via properties or predicates) data elements with one another. Resolvable URIs in domain model 14 ground this model, expressed as RDF, into a web-based network to facilitate its retrieval and management using existing as well as yet-to-be-developed semantic web-based tools.

One or more hierarchical relationships between data elements in domain model 14 are expressed as a core vocabulary term according to the underlying metadata model 12. The term may be called a "core vocabulary term" because it describes the most important relationship between knowledge elements. The core vocabulary and rule set for metadata model 12 enable and facilitate extending and managing the system 10. Those skilled in the art will understand and appreciate that metadata model 12 and its rule set can be applied to any particular domain model 14, which facilitates its extensibility.

System 10 includes a domain model interface element 16 that enables a domain expert to create, extend, or modify domain model 14, expressed via metadata model 12, without requiring assistance of a database expert. Domain model interface element 16 can include a user interface, with graphical or text-based features to enable modifying existing data elements and relationships between data elements as well as to enable addition of new data elements and relationships between new and existing data elements. Those skilled in the art will understand and appreciate various types of graphical features (e.g., pull-down menus, buttons, etc) and text-based features (e.g., text entry fields) that can be employed to enable the modification of the domain model. Changes to domain model 14 can be entered via domain model interface element 16 and transformed to appropriate syntactic form to update the domain model 14 accordingly.

There can be one or more instances of domain model 14 (described herein as a "domain instance" or an "instance of the model"). Instance data for domain model 14 can be stored in a knowledgebase/database repository (or other data storage system) 18, which is configured to store data for system 10. The particular form or structure of repository 18 may vary according to available computer system and other resources in which system 10 is implemented. Domain model 14 can be instantiated with instance data, such as by use of a data entry component (or user interface) 20. The domain instance can correspond to a selected portion of the model, as can be determined by a particular data entry component 20. For example, a data entry component 20 can populate one or more fields of a template or form based on an appropriate portion of instance data. New data can also be entered via a data entry component 20 to modify a given domain instance. Thus, the domain model and each domain instance can be extensible and independently changeable. For instance, domain model 14 can be extended and changed arbitrarily without affecting previously stored instance data as long as that portion of domain model 14 that corresponds to previously stored instance data remains unchanged.

An instance of the given domain model 14 is stored in repository 18 as a domain instance representation 22. There can be any number of one or more instance representations 22, each being an instantiation of the same or a different portion of domain model 14.

By way of example, a domain instance representation 22 can be expressed in a relational model and stored in a relational database. By way of further example, a tree-structured representation of domain instance representation 22 can be serialized as an XML document and further may have a corresponding XML information set. The XML document can be considered to have the XML information set if it is well-formed and satisfies namespace constraints for the domain instance. The domain instance representation (e.g. an XML instance) can be validated by corresponding schema that is associated with the given domain instance. Such a schema can be generated from domain model 14 for the given domain instance embodied in domain instance representation 22. The schema and other data management tools are schematically demonstrated at 24. As described herein, the generation of the data management tools can be triggered automatically in response to completing domain model 14, in response to creation of the domain model, in response to modification of the domain model or any combination thereof.

System 10 includes a domain interpreter 28 that is programmed or configured to manage and interpret domain model 14. Domain interpreter 28 includes one or more tool generators (e.g., functions or methods) 30 programmed to generate one or more data management tools 24 that facilitate interaction, use, and management of domain model 14 and of corresponding domain instance representation 22.

One or more tool generators 30 perform functions to generate data management tools 24 based on a predefined rule set 32 for the metadata model 12. That is, rule set 32 defines how at least hierarchical relationships between data elements in domain model 14 are to be interpreted. Thus, rule set 32 defines a logically consistent means to translate hierarchical relationships between elements into a set of formal constraints. Domain interpreter 28 thus is programmed to translate node metadata of domain model 14 into at least one formal ontology, such as by using at least one of class constructors, role hierarchies, functional restrictions, cardinality restrictions, data types, and transitive roles. The rules can be defined in rule set 32 or be programmed into function/methods implemented by interpreter 28. By way of further example, if domain instance representation 22 is an XML document, tool generator 30 can generate a corresponding XML schema for the given instance of the XML documents by applying rule set 32. In such an example, the XML schema represents logical constraints that can be applied (e.g., by an XML processor) to validate the XML instance of domain model 14.

As used herein, an XML schema defines an XML vocabulary for expressing rules of the domain represented by the model. The XML schema thus includes data constraints or rules that are required for an XML document to be valid. The XML schema specifies contents of each element (structure of instance documents and datatype of each element/attribute), and restrictions on content for each data element. The XML schema specifies that the XML vocabulary that is being created for the domain is stored in a known schema namespace. Elements and attributes defined by the schema are also stored in a corresponding namespace. An XML schema validator thus employs a given XML schema generated for a given model to validate an XML instance of a given model.

In addition, tool generator 30 can apply the rule set 32 to generate a transformation component as one of the data management tools 24. Such a transformation can convert one domain instance representation 22 to a second domain instance representation 34 to provide multiple concurrent instance representations of the same domain model 14. As an example, if the first domain instance representation 22 is an XML document, the transformation can be implemented by using a corresponding extensible stylesheet language transformation (XSLT) to convert the domain instance representation 22 to a second domain instance representation 34, for example, an RDF graph.

By employing such a transformation, multiple instance representations 22 and 34 of the same given domain instance can exist concurrently in system 10. Multiple representation affords advantages of facilitated user entry and manipulation, such as via data entry component 20, and facilitates querying and searching through a given instance representation. As one example, domain instance representation 22 can correspond to an XML instance of domain model 14 and the second domain instance representation 34 can correspond to a more semantic representation, expressed formally in a knowledge representation language such as RDF. Tool generator 30 can also employ rule set 32 to create a data management tool 24 corresponding to a formal ontology (e.g., according to OWL) that is operatively associated with the second domain instance representation 34. The ontology provides a mechanism that can be employed by an intelligent agent that understands RDF and OWL and thus infers new relationships between elements in the RDF graph instance of the domain model. An intelligent agent can be any software agent that exhibits some form of artificial intelligence, such as can assists a user and will act on their behalf, in performing non-repetitive computer-related tasks. Examples of intelligent agents include neural networks, fuzzy logic and expert systems to name a few.

Those skilled in the art will understand and appreciate other types of data management tools 24 that can be generated by domain interpreter 28 based on methods described herein. For example, other tools can include data dictionaries for the domain model, as well as data entry templates, constructed queries, one or more schemas, transformations, and interfaces and report templates. Each of such tools can be associated with a given instance or instance representation of the domain model. Alternatively, some tools can be generic and utilized by different domain instances or instance representations indiscriminately.

Figure 2:
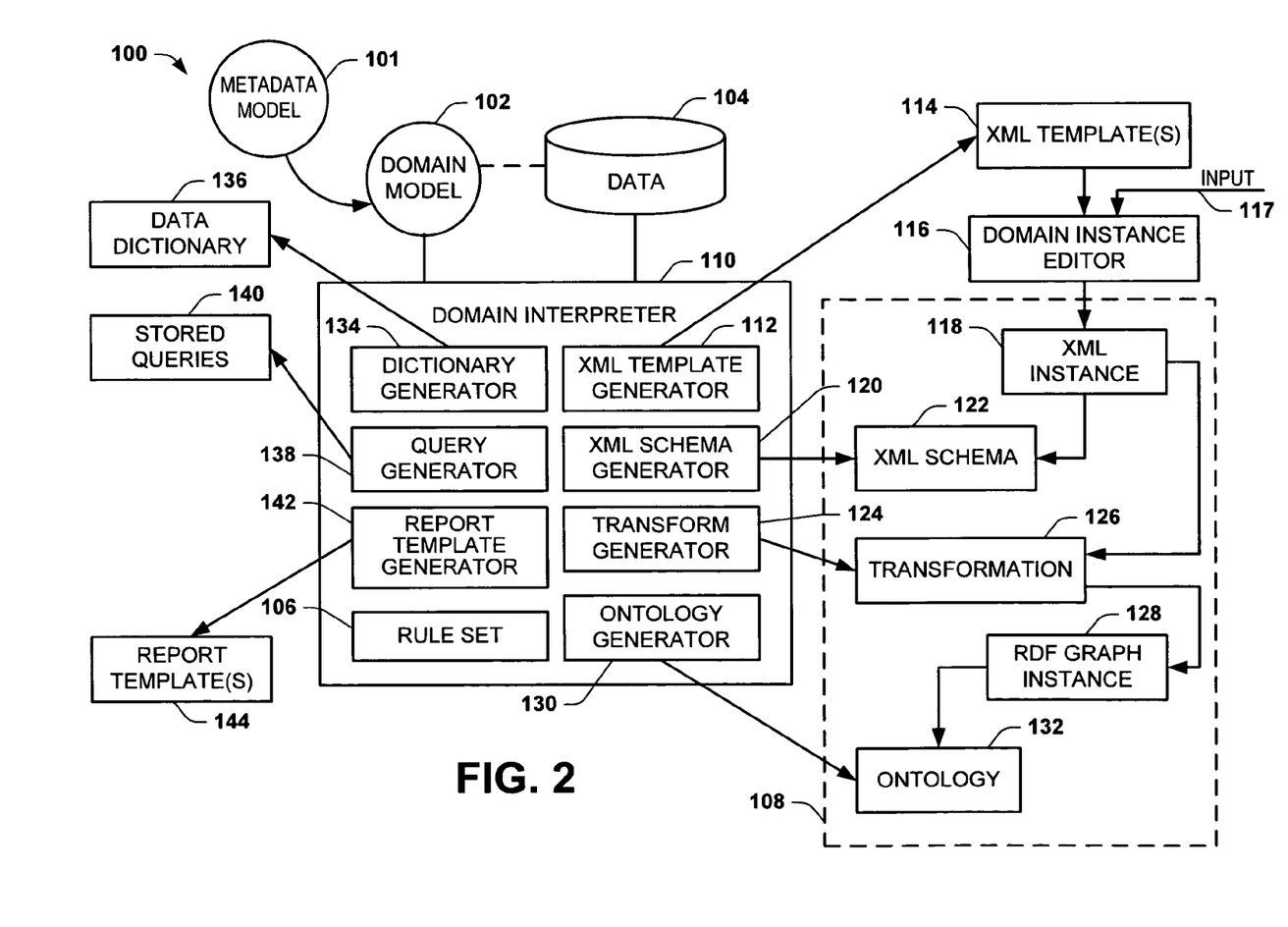
FIG. 2 depicts another example of a database system that can be implemented according to an aspect of the present invention.

FIG. 2 depicts an example embodiment of a knowledgebase/database system 100 that can be implemented according to an aspect of the present invention. FIG. 2 expands on some of the concepts previously described that can be employed to implement system 100 described herein. System 100 includes a domain model 102 that expresses concepts in a domain for which the system has been created. By way of example, the domain can correspond to an enterprise, such as a business or organization, whose knowledge and data can be stored in a corresponding knowledgebase/database repository 104 in one or more physical locations. The particular organization employed to store knowledge and data for the enterprise is expressed by domain model 102 that can vary according to requirements of the enterprise and available resources for system 100. The domain model expresses concepts in the domain according to metadata model 101. Metadata model 101 includes a core vocabulary that expresses predetermined hierarchical relationships among data elements in domain model 102. Rule set 106 expresses logical relationships of metadata model 101.

For example, the relationships between data elements include at least one hierarchical relationship that can be utilized to manage, manipulate, and interpret domain model 102 and instances thereof. One hierarchical relationship represented in metadata model 101 is a containment (or contains) relationship. This relationship with rule set 106 applied defines the contains relationship so that it is expressly interpreted as indicating a parent-child relationship between nodes in domain model 102. The contains relationship can be inherited via RDF properties, including rdfs:subClassOf and :inheritsConstraints properties. For those skilled in the art, the former property defines classic logical subsumption and the latter object-oriented inheritance. As an example, rules in rule set 106 to interpret the contains relationship can be expressed as follows:

{if D :inheritsConstraints A and if A :contains x} then {D contains x}.

{if D rdfs:subClassOf A and if A :contains x}=>{D :contains x}.

{if x rdfs:subClassOf y and if y rdfs:subClassOf z} then {x rdfs:subClassOf z}.

Metadata model 101 can also include class constructors, role hierarchies, functional restrictions, cardinality restrictions, and data types, as well as transitive roles used in domain model 102. As an example, rule set 106 can include core rules that define rdfs:subClassOf and dnode:inheritsConstraints as transitive properties:

{if x rdfs:subClassOf y and if y rdfs:subClassOf z} then {x rdfs:subClassOf z}.

{if x :inheritsConstraints y and if y :inheritsConstraints z} then {x :inheritsConstraints z}.

As a convenience, rule set 106 can also require that children of data that do not fall within the domain but describe how instance data are managed—called process data—are also process data. Rule set 106, for example, can include a rule that defines constraints for process data as follows:

{if x a :ProcessData and if x :contains y} then {y a :ProcessData}.

Rule set 106 is utilized by domain interpreter 110. Domain interpreter 110 includes a plurality of functions or methods that are programmed to generate corresponding data management tools for instances of domain model 102. That is, the particular functions implemented by domain interpreter 110 employ rule set 106 relative to domain model 102 to generate respective data management tools for domain instances. Dashed box 108 is provided to demonstrate an environment by which intelligent agents (software components that follow a plan and adhere to ontological commitment without human intervention) can behave autonomously. Environment 108 will be understood to encompass any number of representations of domain instances as shown and described with respect to FIG. 1, each of which can be similar to that illustrated in FIG. 2.

By way of further example and for sake of consistency, and not by way of limitation, system 100 of FIG. 2 will be described herein in the context of a medical information system with particular examples directed to cardiac dimension data. It will be understood and appreciated, however, that system 100 is not limited to providing a knowledgebase/database for any particular type of information. For instance, system 100 is further appropriate for business systems or any other suitable environment where it is desirable to collect, maintain, manage and view knowledge and data.

Domain interpreter 110 can include an XML template generator 112 implemented as a function or method programmed to generate one or more XML templates 114. XML template 114 serves as a pattern for populating an instance by means of a user interface, such as a domain instance editor 116. The user interface can be employed by a user (e.g., a domain expert) for editing, managing, and modifying one or more domain instance. For example, the XML template generator can employ rule set 106 to generate one or more templates 114 for instances of domain model 102. Fields of an instance corresponding to data in repository 104 can be populated programmatically via corresponding templates. Additionally, or alternatively, a user can enter or modify data in the template via domain instance editor 116. The modified or added data can then be stored as instance data in the repository 104 without modifying domain model 102 itself.

For the example of an XML template 114 suitable for entering data and modifying data in an instance, a corresponding XML instance 118 can be instantiated from domain model 102 and stored in repository 104 based on one or more user inputs, schematically indicated at 117, or such instantiation can be implemented programmatically, as previously described. Thus, a user can employ one or more templates 114 via domain instance editor 116 to create, modify, add to or delete data from XML instance 118. Such changes made to XML instance 118 can be stored in repository 104, such as by updating the knowledgebase/database via appropriate functions in domain instance editor 116. Such functions can be implemented as buttons, drop down menus, or other text-based or graphical user interfaces. An example of part (e.g., a cardiac dimension portion) of an XML template that can be provided for use with an XML instance 118 for a given domain is as follows:

```
<ptrec:CardiacDimension>
    <ptrec:CardiacDimensionSite/>
    <ptrec:CardiacSiteDiameter/>
</ptrec:CardiacDimension>
```

An actual example of a corresponding part of XML instance 118 for this example might be as follows:

```
<ptrec:CardiacDimension>
    <ptrec:CardiacDimensionSite>left atrium</ptrec:CardiacDimensionSite>
    <ptrec:CardiacSiteDiameter>3.20</ptrec:CardiacSiteDiameter>
</ptrec:CardiacDimension>
```

Domain interpreter 110 also includes an XML schema generator 120. XML schema generator 120 corresponds to functions or methods programmed to generate corresponding XML schema 122 that is operatively associated with XML instance 118. XML schema generator 120 generates the XML schema based on rule set 106 for domain model 102. XML schema 122 includes a collection of type definitions and element declarations whose names belong to the predetermined namespace associated with domain for which domain model 102 has been created. For instance, an XML validator (not shown) can employ XML schema 122 to validate that corresponding XML instance 118 conforms to the particular schema in the target XML namespace for the given domain. An example of a part of an XML schema, such as can be produced by the XML schema generator 120 for a cardiac dimension context, is as follows:

```
<wxs:complexType name="CardiacDimensionWXSType">
    <wxs:annotation>
        <wxs:documentation>Cardiac Dimension</wxs:documentation>
    </wxs:annotation>
```

-continued

```
    <wxs:choice maxOccurs="unbounded">
        <wxs:element type="ptrec:CardiacDimensionSiteWXSType"
    name="CardiacDimensionSite" minOccurs="0"/>
        <wxs:element type="ptrec:CardiacSiteDiameterWXSType"
    name="CardiacSiteDiameter" minOccurs="0"/>
    </wxs:choice>
</wxs:complexType>
```

Domain interpreter 110 can also include a transform generator 124 that generates one or more transformations 126. Transform generator 124 can be defined as functions or methods that employ rule set 106 to generate transformation(s) 126 for XML instances 118 of domain model 102. The resulting transformation(s) 126 is operatively associated with each given instance of domain model 102, including the XML instance 118.

By way of further example, transformation 126 can be programmed to convert XML instance 118 to another form. In the example of FIG. 2, the transformation is programmed to convert XML instance 118 to corresponding RDF graph instance 128. Graph instance 128 can include an association with ontology 132 for intelligent agents to follow. As an example, transformation 126 can be expressed in the XSLT language as a stylesheet that performs the conversion via an XSL processor. For instance, a stylesheet contains a set of template rules. A template rule has two parts: a pattern that is matched against nodes in the source tree and a template that can be instantiated to form part of the result tree. By way of example, in transformation 126, a template can be instantiated for a particular source element of XML instance 118 to create part of the result tree corresponding to RDF graph instance 128. A template can contain elements that specify literal result element structure. A template can also contain elements from the XSLT namespace that are instructions for creating result tree fragments. When a template is instantiated for the given domain model, each instruction is executed (e.g., by the XSL processor) and replaced by the result tree fragment that it creates. The result tree is constructed by finding the template rule for the root node and instantiating its template. An example of a portion of an XSLT transformation that can be generated by transform generator 124 for converting part of XML instance 118 to corresponding RDF graph instance (e.g., written in Notation3) 128 is as follows:

```
<xsl:template match='ptrec:CardiacDimension'>
    <xsl:param name='semiColon' select='true( )'/>
    <xsl:variable
        name="explicitType"
        select="true( )"/>
    <xsl:if test="$semiColon">;</xsl:if> :contains
[
    <xsl:if test="$explicitType">
    a <xsl:value-of select="name( )"/></xsl:if>
    <xsl:for-each select='ptrec:CardiacDimensionSite |
    ptrec:CardiacSiteDiameter'>
        <xsl:variable name='childSkipSemiColon' select='position( ) = 1
            and not($explicitType)'/>
        <xsl:choose>
            <xsl:when test='text( )'>
                <xsl:if test="not($childSkipSemiColon)">;</xsl:if>
                <xsl:value-of select="name( )"/>
                <xsl:text> </xsl:text>
                <xsl:apply-templates mode='nodevalue' select='text( )'/>
                <xsl:text> </xsl:text>
            </xsl:when>
            <xsl:otherwise>
                <xsl:apply-templates select='.'>
```

-continued

```
                    <xsl:with-param name='semiColon'
                    select='not($childSkipSemiColon)'/>
                </xsl:apply-templates>
            </xsl:otherwise>
        </xsl:choose>
    </xsl:for-each>
]
</xsl:template>
```

It will be understood and appreciated that RDF instance 128 produced by transformation 126 can be written in a variety of known or yet to-be-developed syntactic forms, such as RDF/XML and N3. It can also be understood and appreciated that existing mechanisms, such as Gleaning Resource Descriptions from Dialects of Language (GRDDL), can benefit from transformation 126 generated from transform generator 124. This can facilitate external intelligent agents in processing knowledge and data in repository 104. An example of a portion of an RDF graph that can be produced by applying the above XSLT transformation to the example XML instance (as set forth above) is as follows:

a ptrec:CardiacDimension;

ptrec:CardiacDimensionSite "left atrium";

ptrec:CardiacSiteDiameter "3.20"^^xs:float

As a result of applying transformation 126 to the XML instance, system 100 can concurrently provide multiple instance representations of given domain model 102, which can be used to leverage the advantages of the different types of instance representations. For example, XML instance 118 provides a more robust representation for a variety of applications, such as creating a user interface for modifying these instances based upon user inputs via domain instance editor 116. In contrast, RDF graph instance 128 has more robust semantic attributes that facilitate querying, inferences, and other uses by a variety of applications that understand knowledge representation.

XML instance 118 corresponds to a tree-structured XML graph that can be employed as an extensible data structure. For example, domain instance editor 116 or other functions can add to or modify data in repository 104 that is associated with XML instance 118 based on user inputs. As XML instance 118 is modified, such modification can be propagated to RDF graph instance 128.

In order to facilitate use of RDF graph instance 128, domain interpreter 10 also includes an ontology generator 130. Ontology generator 130 is programmed with functions or methods that employ rule set 106 to generate a corresponding ontology 132 for RDF graph instance 128. Ontology 132 explicitly represents the meaning of terms in vocabularies and the relationships among those terms for use by one or more applications that understand the ontology language used. For instance, ontology 132 can be employed for performing validation of RDF graph instance 128. Ontology 132 also enables interpreting and drawing relationships (inferencing) by appropriate applications via RDF graph instance 128.

As one example, the ontology can be generated according to OWL, a markup language employed for publishing and sharing knowledge using ontologies. OWL can be utilized to define everything known about each data node that represents a fundamental class in the domain model. For instance, a fundamental data node is defined as an OWL class, which can then be subclassed by various, more specific data node classes. OWL has more facilities for expressing meaning and semantics than typically expressed in XML instance 118 or RDF graph instance 128. Thus, ontology 132 (whether represented in OWL or another ontology language) provides machine-interpretable content that enables and facilitates use (e.g., by one or more applications or methods) of RDF graph instance 128 to which it is associated. An example of a portion of classes and properties specific to an OWL ontology for the cardiac dimension example that can be generated by ontology generator 130 is as follows:

```
<owl:Class rdf:about="#CardiacDimension">
    <rdfs:label>Cardiac Dimension</rdfs:label>
    <rdfs:subClassOf rdf:resource="#EchocardiogramData"/>
</owl:Class>
<owl:DatatypeProperty rdf:about="#CardiacDimensionSite">
    <rdfs:comment>Refers to the cardiac site where the measurement was
taken.</rdfs:comment>
    <rdfs:domain rdf:resource="#CardiacDimension"/>
    <rdfs:range rdf:resource="http://www.w3.org/2001/
XMLSchema#string"/>
</owl:DatatypeProperty>
<owl:DatatypeProperty rdf:about="#CardiacSiteDiameter">
    <rdfs:comment>Refers to systolic or diastolic diameter
(cm).</rdfs:comment>
    <rdfs:domain rdf:resource="#CardiacDimension"/>
    <rdfs:range rdf:resource="http://www.w3.org/2001/
XMLSchema#float"/>
</owl:DatatypeProperty>
```

Domain interpreter 110 can also include functions or methods to facilitate other enterprise-based operations that may be performed relative to given domain model 102. For example, domain interpreter 110 can include data dictionary generator 134 that is programmed to generate a data dictionary 136 based on rule set 106. For instance, the data dictionary can include a thesaurus, conversions for other languages as well as other relevant terms and vocabularies that may be utilized by a (human) data manager.

Domain interpreter 110 can also include query generator 138 that is defined by functions or methods that generate one or more stored queries 140 based on predetermined rule set 106 associated with domain model 102. Query generator 138 can generate stored queries 140 in a variety of query languages such as XPath, SPARQL, Versa, and XQuery.

Stored queries 140 further can be applied to one or more of XML instance 118 and RDF graph instance 128 such as for querying the instance for information contained therein, as well as to facilitate investigative research. For example, one or more of stored queries 140 can include a SPARQL query associated with RDF graph instance 118 that can be utilized in conjunction with ontology 132.

As another example, a stored query 140 can be a predefined query for identifying an instance of a particular data element in RDF graph instance 128 or XML instance 118. The particular form of query thus can depend upon which instance 118 or 128 is best suited for extracting knowledge or data from repository 104. It is to be understood and appreciated that, in other instances, ontology 132 may provide an adequate mechanism for acquiring certain information from RDF graph instance 128 that may be used in addition to or as an alternative to a stored query 140.

Domain interpreter 110 can further include a report template generator 142 that is programmed to generate one or more report templates 144 based on rule set 106. Report template generator 142, for example, can include functions or methods preprogrammed to generate one or more reports useful in displaying results of one more of stored queries 140, as well as displaying in one or more formats XML instance 118 and RDF graph 128. As a further example, an XSLT processor employing the template as a predetermined XSLT stylesheet can convert the XML instance (or a selected portion thereof) into a corresponding report in an appropriate human-readable format (e.g., text, PDF, CSV).

Those skilled in the art will understand and appreciate various other types of tools that might be generated for a given domain model 102. Additionally, although a single combination of domain instances 118 and 128 was shown and described in the example of FIG. 2, it is to be appreciated that there can be any number of one or more such combinations. It will be understood and appreciated that there can be overlap between two or more of the tools (e.g., transformation 126 and report templates 144). For instance, tools can share common functions or templates that are generated by domain interpreter 110 for given domain model 102. Additionally or alternatively, the data management tools, such as the data dictionary 136, stored queries 140, and report templates 144, can be generically applicable to multiple instance of the domain model 102.

Figure 3:
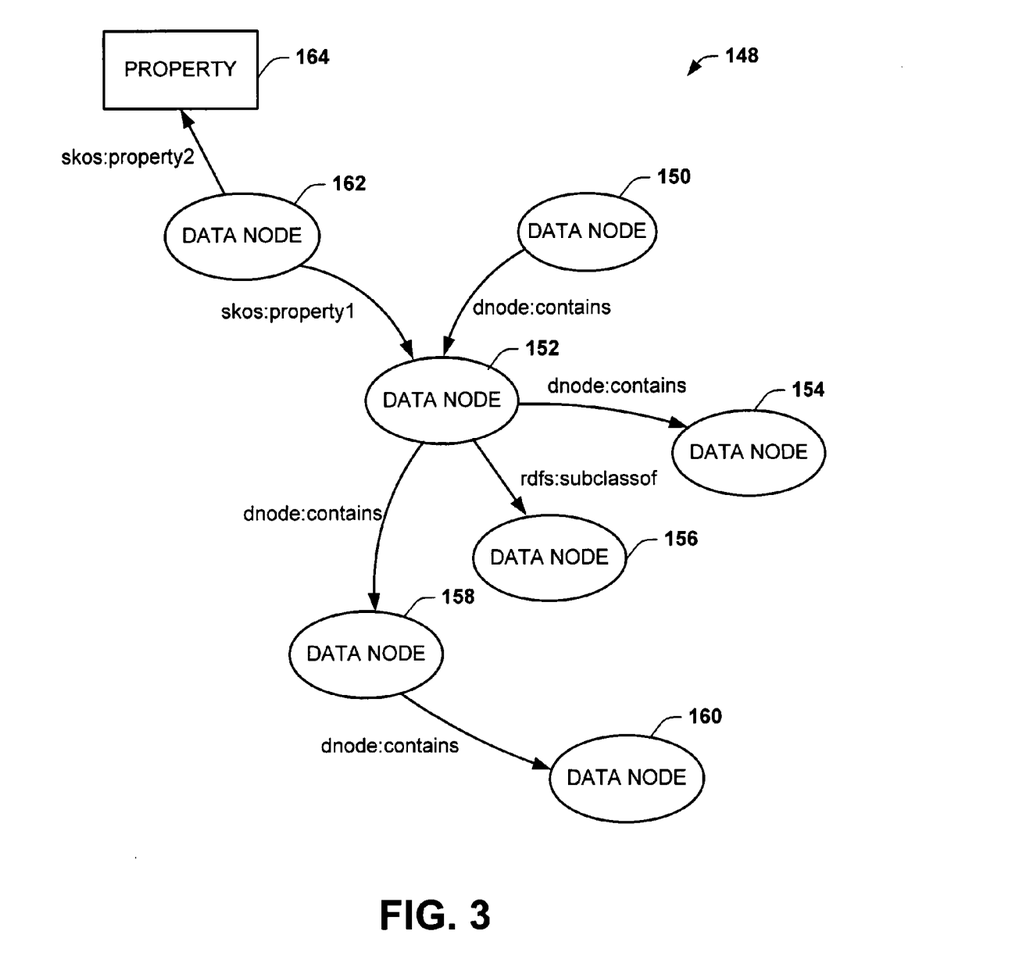
FIG. 3 depicts an example of a Resource Description Framework (RDF) representation of a metadata model that can be implemented according to an aspect of the present invention.

FIG. 3 depicts an example of a metadata model 148 that can be employed to express concepts in a domain. Metadata model 148 is depicted as an RDF graph that includes nodes, indicated by ellipses, and relationships, indicated by arcs. As mentioned above, concepts for the domain can be expressed as FOPL, although other logic constructs could also be utilized.

In example of FIG. 3, root node 150 contains data node 152. Thus, as described herein, node 150 is explicitly interpreted as having a parent-child relationship with node 152. Node 152 is associated with nodes 154 and 158 via the contains relationship. Model 148 also establishes node 156 as a subclass of node 152. Node 158 is associated with node 160 via the contains relationship.

To facilitate practical application of the model 148, it can also include nodes and relationships that represent annotative properties, such as via Simple Knowledge Organization System (SKOS) properties. SKOS is family of formal languages designed for representation of thesauri, classification schemes, taxonomies, subject-heading systems, or any other type of structured controlled vocabulary. Use of SKOS properties in model 148 can employ any SKOS components, including SKOS core, mapping, and extensions. Each SKOS concept can be defined as an RDF resource. The SKOS core component, for instance, can represent common features found in standard thesauri. It can also include a vocabulary organized in hierarchies using broader-narrower relationships, or linked by non-hierarchical (associative) relationships. Additional information about SKOS components has been defined, and is being developed, by the Semantic Web Deployment Working Group of the World Wide Web Consortium (W3C).

For example, node 162 can be related to node 152 via a predetermined SKOS property (skos:property1). Node 162 further can be related to annotative node 164 via the annotative property skos:property2. Those skilled in the art will understand and appreciate various other properties and constraints that can be employed in metadata model 148 to support desired structural (e.g., datatype constraints, hierarchical constraints, cardinality constraints and the like) and semantic (e.g., thesauri, descriptive logics, and the like) relationships based on the teachings contained herein. As one example, the model can represent cardinality (multiplicity) of a data element, which establishes the number of times that instances of a data node are required or permitted to occur. This can be indicated as maxOccurs and minOccurs, as used in XML schema. Data value constraints can further be employed to restrict values that instances of a data node can assume.

Figure 4:
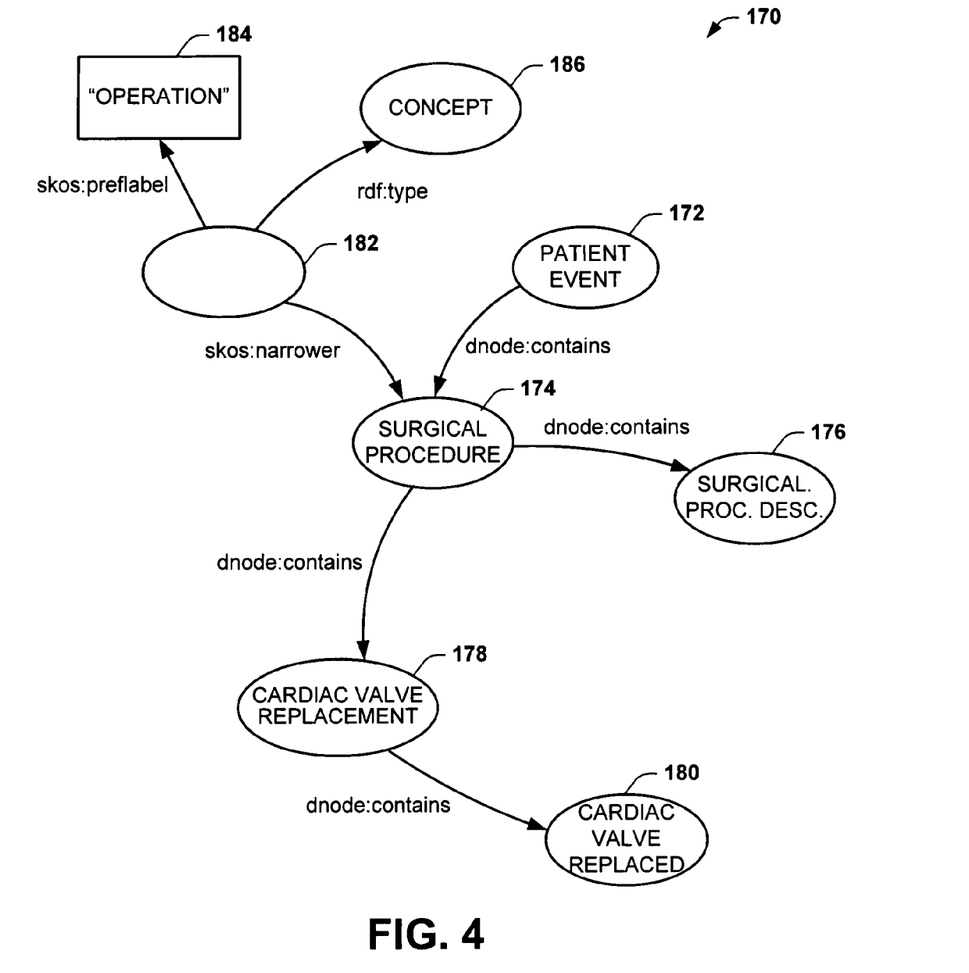
FIG. 4 is an example RDF graph representation of a domain model that can be provided based on the metadata model of FIG. 3 according to an aspect of the present invention.

FIG. 4 depicts an example of a domain model 170 that can be provided based on the metadata model of FIG. 3. FIG. 4 is an RDF graph of certain concepts in a medical information domain. Each data node represents a class of concepts that could be instantiated in a knowledgebase/database of medical records. It will be understood, however, that the present invention is not limited to any type of domain or to any class of concept that can be expressed for a given domain.

Model 170 thus includes root node 172, designated as "patient event." Node 172 further contains node 174, designated as "surgical procedure." For instance, surgical procedure node 174 can be instantiated as an instance of the class "surgical procedure," such as a valve replacement, which is contained by an instance of the root node 172. Node 174 contains both nodes 176 and 178 designated as "surgical procedure description" and "cardiac valve replacement," respectively. Node 178 contains node 180, which is designated as "cardiac valve replaced."

Domain model 170 also includes annotative properties via blank node 182. Node 174 "surgical procedure" is identified as being a narrower type of "operation." Node 182 is a skos: Concept, as indicated by the rdf:type relationship to node 186. The skos:Concept, for example, can correspond to a mapping component that is employed to express matching (exact or fuzzy) of concepts from one concept scheme to another; for instance, "surgery" can be indicated as a synonym for "operation."

Figure 5:
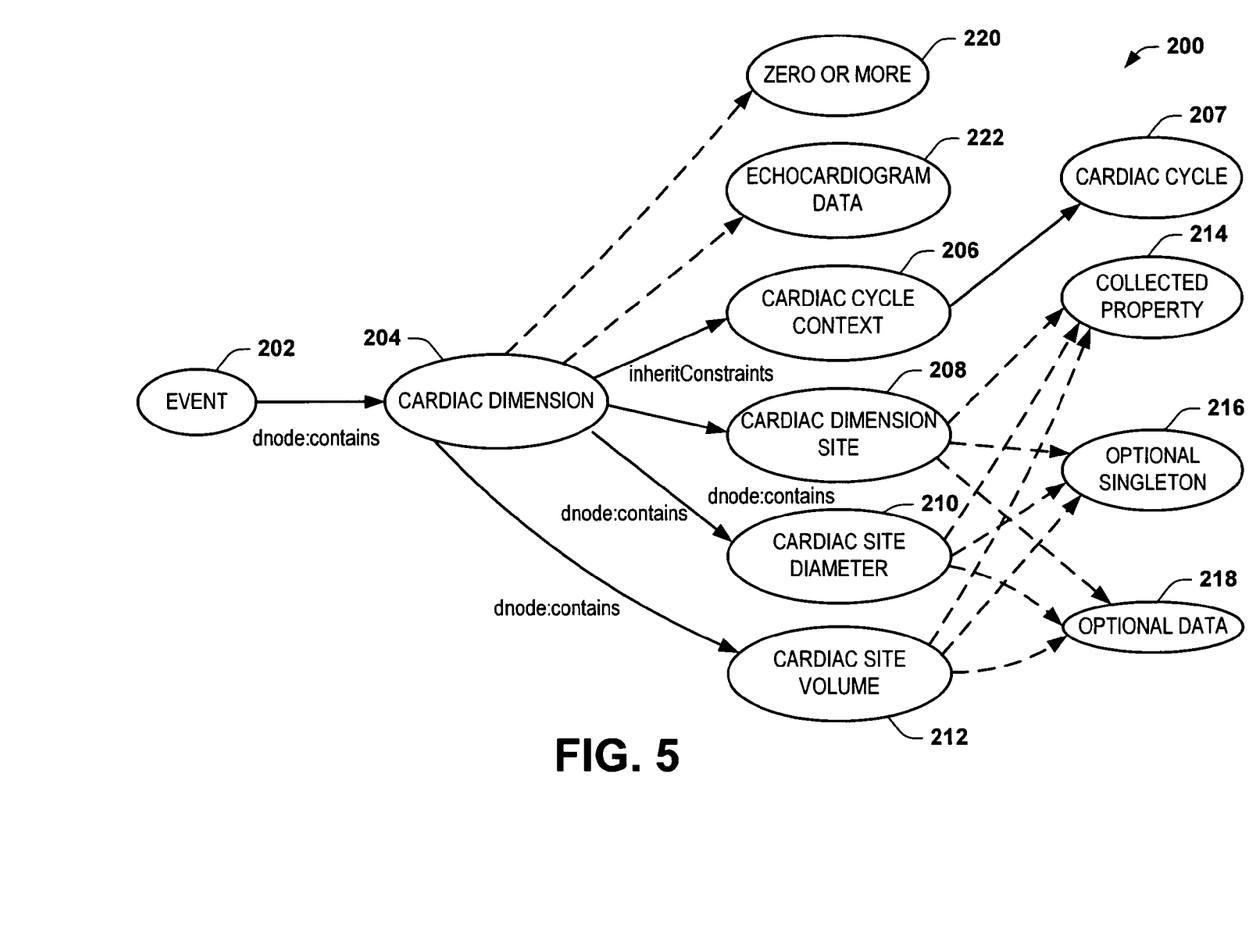
FIG. 5 depicts an example of an RDF representation of part of a domain model that can be implemented according to an aspect of the present invention.

FIG. 5 depicts an example of an RDF graph representation of a domain model 200 that can represent cardiac dimension knowledge associated with an event. In particular, domain model 200 includes event node 202 associated with cardiac dimension node 204 via the contains relation. Cardiac dimension node 204 further contains nodes, 208, 210 and 212. Node 208 represents a cardiac dimension site, node 210 a cardiac site diameter, and node 212 a cardiac site volume. These cardiac dimensions are specific for a designated portion of the cardiac cycle given in instances of node 207. Node 204, by virtue of the inheritsConstraints relationship with 206, also contains cardiac cycle node 207, such as can be established by a corresponding rule set as described herein. Nodes 208, 210 and 212 are subclasses of nodes 214, 216, and 218 via the rdfs:subClassOf relationship, indicated by dashed, directed arcs. That is, each node 208, 210 and 212 is a collected property (via node 214), an optional singleton (via node 216), and optional data (via node 218). Rules for the database system thus define how the structural and semantic relationships between nodes are interpreted. Cardiac dimension node 204 further is echocardiogram data of cardinality zero or more via the rdfs:subClassOf relationship, indicated by dashed lines from node 204 to nodes 220 and 222.

Figure 6:
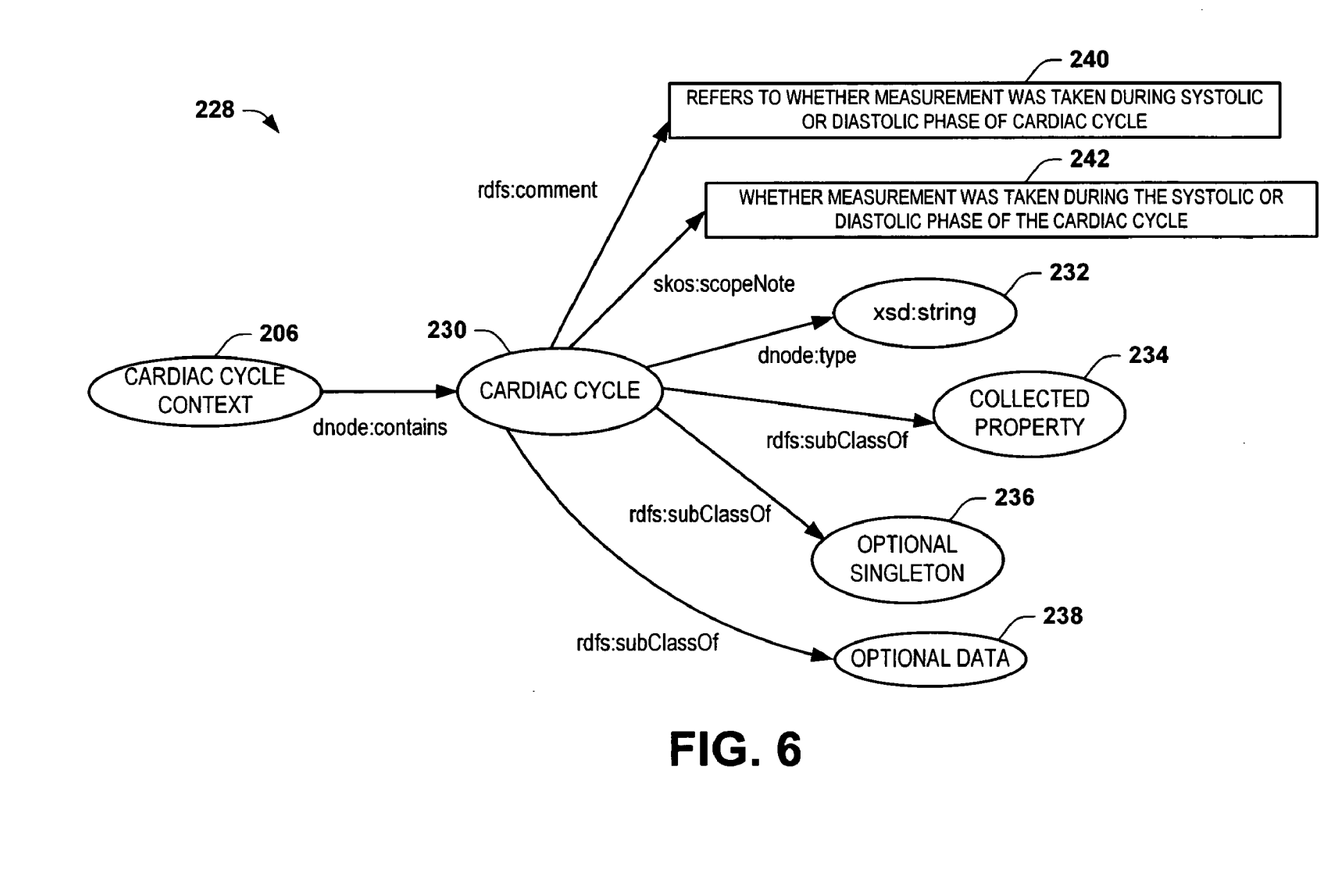
FIG. 6 depicts an example of an RDF representation of part of the RDF representation of FIG. 5 that can be implemented according to an aspect of the present invention.

Cardiac cycle context node 206 is expanded in RDF graph domain model representation 228 shown in FIG. 6. Cardiac cycle context node 206 contains cardiac cycle node 230 via the contains relationship. Cardiac cycle node 230 is represented as having as a data type relationship (dnode:type) that can be an xsd:string, such as can be defined by XML schema rules to which a valid XML document must conform. Cardiac cycle node 230 is a collected property, an optional singleton, and optional data via the subclass relationships to nodes 234, 236 and 238.

As mentioned above, annotations such as comments and dictionaries can also be useful for extending the database for a given domain. As an example, comments can be provided via the rdfs:comment 240, to help the user edit instance data appropriately. A skos:scopeNote 242 can also be provided to indicate similar, but more concise, notations. Both can indicate that a measurement was taken during the systolic or diastolic phase of the cardiac cycle. Those skilled in the art will understand and appreciate various types of data that can be expressed in a domain model in accordance with an aspect of the present invention.

Figure 7:
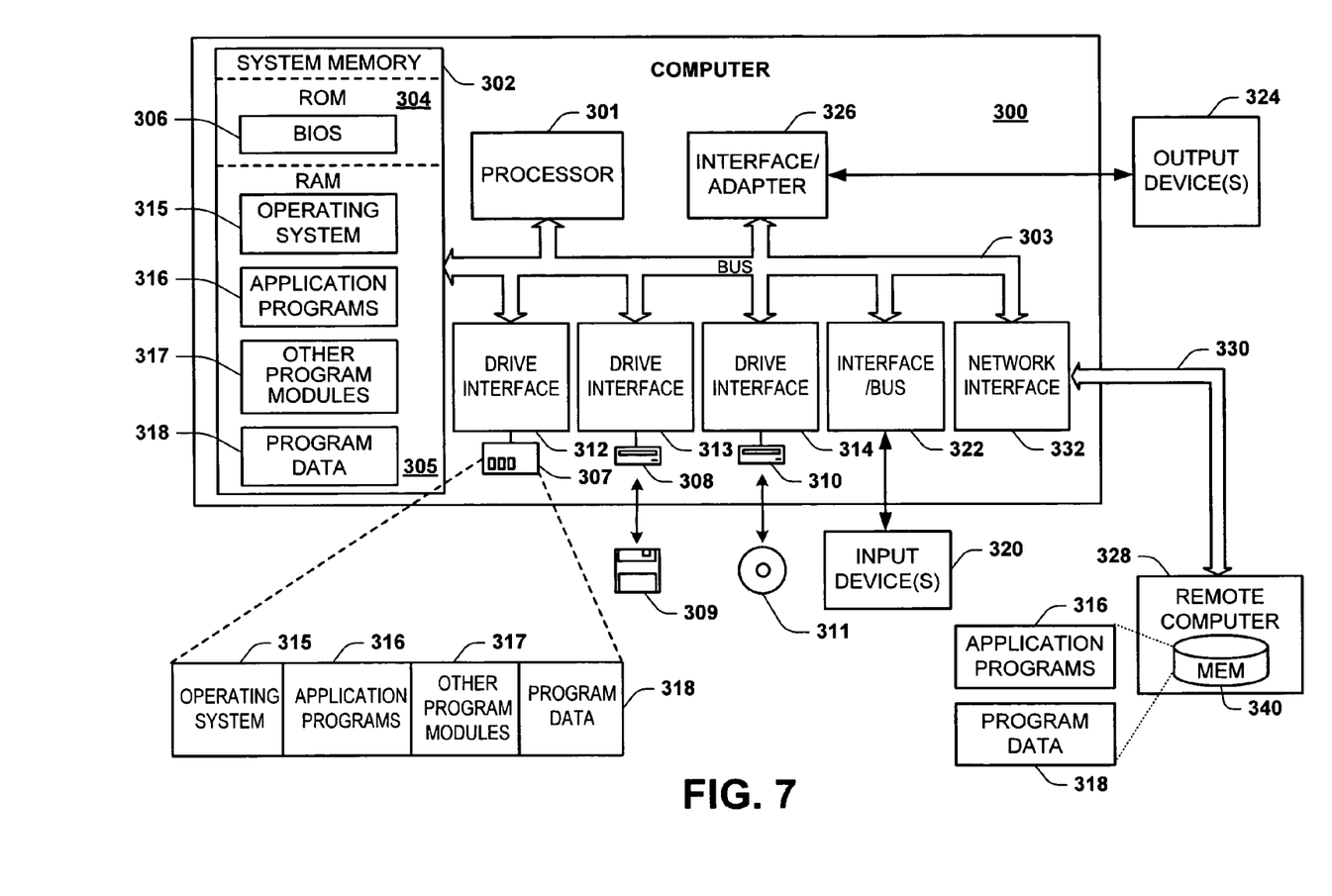
FIG. 7 depicts an example computer system that can implement a database system according to an aspect of the present invention.

FIG. 7 illustrates computer system. 300 that can be employed to execute one or more embodiments of the invention employing computer executable instructions. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a cell phone, personal digital assistant (PDA), laptop computer, pager, and the like.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the present invention.

A number of program modules may be stored in drives and RAM 305, including operating system 315, one or more application programs 316, other program modules 317, and program data 318. The application programs and program data can include functions and methods programmed to implement a knowledgebase/database system (or portions thereof) based on the teachings contained herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. Additionally or alternatively, a user can access a user interface via the input device to create one or more instances of a given domain model and associated data management tools, as described herein. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 8:
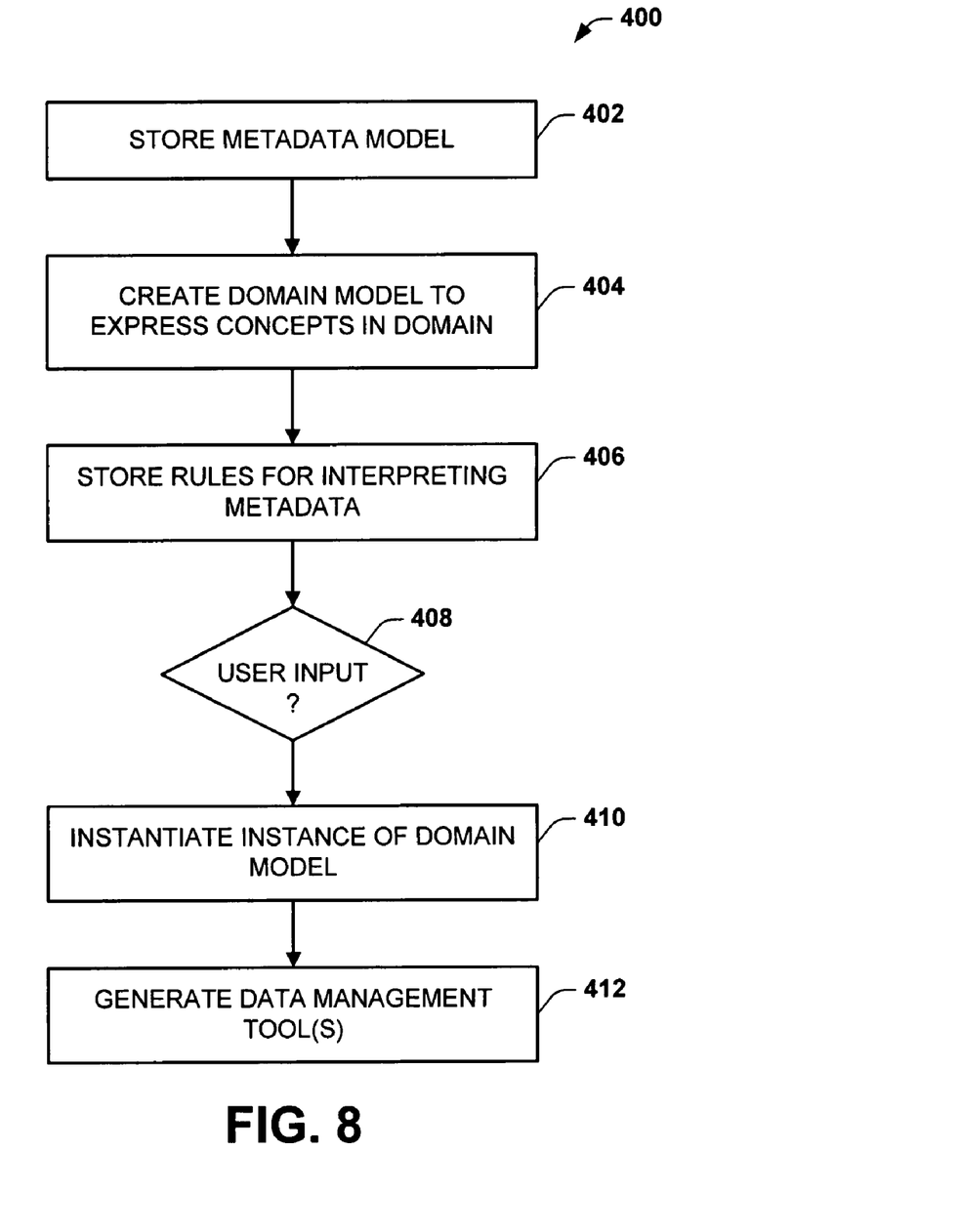
FIG. 8 is a flow diagram illustrating method for implementing a database system according to an aspect of the present invention.

In view of the structural and functional features described above, certain methods will be better appreciated with reference to FIG. 8. It is to be understood and appreciated that the illustrated actions, in other embodiments, may occur in different orders or concurrently with other actions. Moreover, not all features illustrated in FIG. 8 may be required to implement a method. It is to be further understood that the following methodology can be implemented in hardware (e.g., one or more processors, such as in a computer or computers), software (e.g., stored in a computer readable medium or as executable instructions running on one or more processors), or as a combination of hardware and software (see, e.g., FIG. 7).

FIG. 8 is a flow diagram illustrating method 400 for providing an extensible knowledgebase/database, such as described herein. At 402, the method includes storing a metadata model.

At 404, a domain model is created to express concepts for a desired domain according to metadata model 402. Domain model can be stored at 404, such as in a repository, according to the teachings contained herein. Metadata for domain model defines at least one hierarchical relationship between data elements in the domain model. Domain model, for example, can be a graph model representation (e.g., a directed acyclic graph) in which data elements of the domain model comprise nodes and arcs interconnecting pairs of nodes, where the nodes are classes within the domain and arcs represent relationships between them. This domain can be expressed according to a formal knowledge representation language (e.g., RDF). For a graph model representation, domain model can include a core vocabulary term that defines a "contains" relationship, which is explicitly interpreted as indicating a parent-child relationship between nodes in the graph model representation of the domain model.

At 406, predetermined rules for interpreting metadata are stored. The rules establish a consistent logical interpretation that can be employed to process domain model (stored at 404) in a variety of ways. For instance, the rules can express descriptive logic semantics.

At 408, one or more user input can be received. At 410, domain model can be instantiated to provide one or more domain instances for user input provided at 408. Instantiation of at least a portion of domain model can be facilitated by templates generated by interpreting rules and metadata (stored at 406). As discussed herein, domain model can be extended independently from the domain instance, and the instance can be modified independently from domain model 404. Thus, a user can add instance data or otherwise modify the instance independently from domain model (created at 404) based on entering data into an appropriate interface at 408. As described herein, domain instance 410 can be expressed as a tree-structured representation (e.g., an XML information set).

At 412, one or more data management tool can be generated based on stored rules and be associated with domain instance (generated at 410). For example, the knowledgebase/database system can include an interpreter with functions or methods programmed to generate data management tools at 412. The generation of such tool(s) can be performed automatically (by an interpreter based on rules stored at 406) in response to the instantiation of the at least a portion of domain model as well as in response to other operations on the domain model, such as creating or modifying the domain model. The data management tool(s) can include, but is not limited to, a formal ontology, an XML schema, a data dictionary, a data transform, a report template, and a constructed query or any combination thereof.

As described herein, more than one representation of a given domain instance can exist concurrently. For example, a first representation of domain instance can be expressed as an XML instance and a second instance can be expressed according to a formal knowledge representation language (e.g., RDF). For example, rules stored at 406 can be utilized by an interpreter to generate one of the tools (at 412) to transform the first representation to a concurrent second representation. The transformation can be generated and associated with the given domain instance by one or many mechanisms, including GRDDL.

Described above are examples of the present invention. It is, of course, not possible to describe every conceivable combination of components or methodologies of the present invention, but one of ordinary skill in the art will recognize that many further combinations and permutations of the present invention are possible. Accordingly, the present invention is intended to embrace all such alterations, modifications, and variations that fall within the spirit and scope of the appended claims. In the claims, unless otherwise indicated, the article "a" is to refer to "one or more than one".

What is claimed is:

1. An extensible database system comprising:
   a processor;
   a data storage system;
   a metadata model arranged to express concepts in a domain as a domain model, the domain model comprising domain elements and at least one hierarchical relationship between data elements, the domain model comprising node metadata that defines relationships between domain elements and properties of at least some of the domain elements;
   the domain model being instantiated to provide at least one XML instance representation of the domain model, the at least one XML instance representation comprising instance data stored in the data storage system;
   a domain interpreter that employs predetermined rules that express logical relationships of the metadata model, the domain interpreter comprising a transform generator that employs the predetermined rules relative to the domain model to generate a transformation for the XML instance representation of a given instance the domain model based on the node metadata from the domain model, the transformation generating a second representation of the given instance of the domain model based on the XML instance representation, wherein the second representation of the given instance of the domain model is expressed as a graph according to a formal knowledge representation language; and a user interface associated with the domain model and configured to at least one of create, view and modify each instance representation of the domain model, wherein additions and modifications to at least the XML instance representation of the domain model are stored in the data storage system.

2. The system of claim 1, wherein the domain model is represented according to a formal knowledge representation language expressing the domain model as a predicate logic.

3. The system of claim 2, wherein the domain model further comprises a graph model representation in which the data elements of the domain model comprise a plurality of nodes and arcs, interconnecting pairs of nodes, representing at least the at least one hierarchical relationship according to the formal knowledge representation language.

4. The system of claim 1, wherein the domain interpreter employs the predetermined rules to generate at least one data management tool that is associated with the at least one instance representation of the domain model.

5. The system of claim 4, wherein the at least one data management tool is programmed to express domain model constraints in at least one instance representation of the domain model based on the node metadata associated with the data elements of the domain model.

6. The system of claim 5, wherein the domain model constraints comprise at least two of cardinality, inheritance, data types, annotations, and vocabulary synonyms.

7. The system of claim 4, wherein the predetermined rules further comprise a set of rules to translate from the at least one hierarchical relationship between the data elements in the domain model, corresponding to nodes in a graph that represent the domain model, to provide the XML instance representation thereof.

8. The system of claim 4, wherein one of the predetermined rules for the domain model defines the at least one hierarchical relationship as including a contains relationship that is explicitly interpreted by the domain interpreter as indicating a parent-child relationship between nodes in the domain model.

9. The system of claim 4, wherein the at least one data management tool further comprises at least one of a formal ontology, schema, data dictionary, transformation, report template, and constructed query.

10. The system of claim 4, wherein the at least one data management tool further comprises an XML schema corresponding to at least a portion of the domain that represents logical groupings of the data elements within the XML instance representation of the domain model.

11. The system of claim 7, wherein the XML instance representation of the domain model is expressed as having a corresponding XML information set.

12. The system of claim 4, wherein the at least one data management tool further comprises at least one formal ontology that employs at least one of class constructors, role hierarchies, functional restrictions, cardinality restrictions, data types, and transitive roles.

13. The system of claim 1, wherein at least the XML instance representation and the second representation of the given instance of the domain model exist concurrently.

14. The system of claim 1, wherein the domain interpreter further comprises an ontology generator programmed to employ the predetermined rules to generate a formal ontology that is associated with the second representation of the given instance of the domain model, the formal ontology explicitly representing meanings of terms and relationships among terms in the second representation of the given instance.

15. The system of claim 1, the domain interpreter further comprising a schema generator that generates a schema based on the node metadata from the metadata model for validating the XML instance representation of the domain model.

16. A computer-implemented method comprising computer-executable instructions for providing an extensible knowledgebase/database, the method comprising:

storing a metadata model programmed to express concepts in a given domain as a domain model, the domain model comprising domain elements;

storing metadata for the domain model in a data storage system, the stored metadata for the domain model defining at least one hierarchical relationship between the data elements in the domain model, the metadata also defining properties of at least some of the domain elements;

storing predetermined rules for interpreting the stored metadata for the domain model;

instantiating at least a portion of the domain model as a to provide a given domain instance, the domain model and the given domain instance being extensible and being independently changeable from each other;

generating a predetermined transformation operatively associated with the given domain instance based on the predetermined rules and the stored metadata for the domain model, the predetermined transformation being programmed to transform a tree-structured representation of the given domain instance to a corresponding graph representation of the given domain instance based on the metadata stored for the domain model; and employing a user interface to at least one of create, view and modify the given domain instance.

17. The method of claim 16, wherein the domain model is represented according to a knowledge representation language for expressing the domain model as predicate logic.

18. The method of claim 16, wherein the domain model further comprises a graph model representation of the domain model in which the data elements of the domain model comprise a plurality of nodes and arcs, interconnecting pairs of nodes, representing hierarchical relationships among nodes in the graph model representation of the domain model according to a formal knowledge representation language.

19. The method of claim 18, further comprising employing at least one of the predetermined rules to interpret a core vocabulary term that defines a contains relationship indicating a parent-child relationship between nodes in the graph model representation of the domain model.

20. The method of claim 19, further comprising employing the predetermined rules to interpret the at least one hierarchical relationship between the data elements in the graph model representation of the domain model to express the given domain instance of the domain model as the tree-structured representation thereof.

21. The method of claim 19, further comprising generating at least one data management tool based on the predetermined rules, the at least one data management tool being associated with the given domain instance.

22. The method of claim 21, further comprising triggering automatic generation of the at least one data management tool in response to at least one of completing, creating or modifying of the domain model.

23. The method of claim 22, wherein the at least one data management tool further comprises at least one of a formal ontology, XML schema, data dictionary, data transform, report template, and constructed query.

24. The method of claim 16, wherein the tree-structured representation of the given domain instance of the domain model is expressed as an XML information set.

25. The method of claim 23, further comprising translating metadata associated with nodes of the domain model into a formal ontology to facilitate use of the graph representation of the given domain instance of the domain model, the formal ontology comprises at least one of class constructors, role hierarchies, functional restrictions, cardinality restrictions, data types and transitive roles.

26. The method of claim 16, wherein the graph and tree-structured representations of the given domain instance of the domain model exist concurrently.

27. The method of claim 23, further comprising:
generating at least one of an ontology or schema that is associated with the given domain instance; and
employing the at least one of an ontology or schema to validate at least one of the graph and tree-structured representation of the given domain instance.

28. A knowledgebase/database system for a medical information domain, comprising:
a processor;
a storage system that comprises:
a metadata model expressing concepts in the medical information domain according to stored data, the metadata model comprising elements related to the medical information domain and metadata that defines relationships between the elements, and
at least one hierarchical relationship between the elements in the metadata model corresponding to a predetermined core vocabulary term for the metadata model;
at least one user interface programmed for managing the metadata model based on user instructions;
at least one given domain instance of the metadata model being generated and stored in the storage system in response to the user instructions wherein the at least one given domain instance comprises a first domain instance representation; and
a transformation programmed to convert the first domain instance representation into a second domain instance representation based on the metadata for the metadata model, the second domain instance representation existing concurrently with the first domain instance representation such that changes to data in the storage system associated with the first domain instance representation are propagated to the second domain instance representation.

29. The system of claim 28, further comprising an interpreter programmed to generate at least one tool for managing or modifying at least one of the given domain instance or the metadata model.

30. The system of claim 29, further comprising a predetermined rule set for the metadata model stored in the storage system, the interpreter employing the predetermined rule set to control generating the at least one tool by the interpreter, at least one rule in the predetermined rule set defining a core vocabulary term for interpreting at least one hierarchical relationship among data elements in the metadata model.

31. The system of claim 1, wherein the domain interpreter further comprises a template generator programmed to generate at least one XML template based on the predetermined rules, the XML template serving as a pattern for populating the XML instance representation of the domain model.

32. The system of claim 1, wherein the transform generator generates the transformation as a stylesheet that includes a set of template rules and instructions programmed for converting part of the XML instance representation to the second representation of the given instance of the domain model, corresponding to an RDF graph instance.

33. The system of claim 1, wherein the domain comprises a medical information domain.

34. The method of claim 16, wherein the tree-structured representation of the given domain instance comprises an XML document, and the graph representation of the given domain instance comprises an RDF graph representation thereof.

35. The system of claim 28, wherein the first domain instance representation comprises a tree-structured representation of the given domain instance, serialized as an XML document, and the second domain instance representation comprises a RDF graph representation of the given domain instance.

* * * * *